United States Patent
Patil et al.

(10) Patent No.: US 11,384,052 B2
(45) Date of Patent: Jul. 12, 2022

(54) AMPHIPHILIC CYCLOHEXYLBENZENE COMPOUNDS DERIVED FROM ALPHA OLEFINS OR VINYLIDENE ALPHA OLEFIN DIMERS

(71) Applicant: ExxonMobil Chemical Patents Inc., Baytown, TX (US)

(72) Inventors: Abhimanyu O. Patil, Westfield, NJ (US); Satish Bodige, Wayne, NJ (US); Arben Jusufi, Belle Mead, NJ (US); Shane Deighton, Bound Brook, NJ (US); Kanmi Mao, Basking Ridge, NJ (US); Alan A. Galuska, Huffman, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/003,475

(22) Filed: Aug. 26, 2020

(65) Prior Publication Data
US 2021/0070702 A1    Mar. 11, 2021

Related U.S. Application Data

(60) Provisional application No. 62/898,172, filed on Sep. 10, 2019.

(51) Int. Cl.
*C07C 309/73* (2006.01)

(52) U.S. Cl.
CPC ........ *C07C 309/73* (2013.01); *C07C 2601/14* (2017.05); *C07C 2601/16* (2017.05)

(58) Field of Classification Search
None
See application file for complete search history.

(56) References Cited

U.S. PATENT DOCUMENTS

| | | | | |
|---|---|---|---|---|
| 7,256,306 B2 * | 8/2007 | Dado | ...... | C07C 303/22 562/30 |
| 7,598,414 B2 * | 10/2009 | Campbell | ...... | C07C 309/31 562/45 |
| 8,076,272 B2 * | 12/2011 | Howes | ...... | C07C 303/32 507/259 |
| 2009/0163669 A1 * | 6/2009 | Sinquin | ...... | C07C 303/06 525/343 |
| 2021/0070699 A1 | 3/2021 | Patil et al. | ...... | C07C 303/06 |

FOREIGN PATENT DOCUMENTS

WO    WO2009/085964    7/2009    ........ C07C 309/31

OTHER PUBLICATIONS

Favre, J. (1955) "Synthesis for detergent additives for lubricants. II. Study by infrared absorption spectrometry", in *Rev. Inst. Franc. Petrole*, v.10, pp. 470-476.

Hajipour, A. R. et al. (2004) "A Novel Method for Sulfonation of Aromatic Rings with Silica Sulfuric Acid," *Tetrahedron Letters*, v. 45(35), pp. 6607-6609.

* cited by examiner

*Primary Examiner* — Brian J Davis

(57) ABSTRACT

Compositions comprising a sulfonated reaction product or a salt thereof may be prepared from a cyclohexylbenzene compound that has been alkylated with an olefin of formula $R^1R^2CCH_2$, wherein $R^1$ is a $C_6$-$C_{24}$ hydrocarbyl group, and $R^2$ is H or a $C_6$-$C_{24}$ hydrocarbyl group. Methods for sulfonating an alkylated cyclohexylbenzene compound prepared from a cyclohexylbenzene compound that has been alkylated with an olefin of formula $R^1R^2CCH_2$, wherein $R^1$ is a $C_6$-$C_{24}$ hydrocarbyl group, and $R^2$ is H or a $C_6$-$C_{24}$ hydrocarbyl group may comprise contacting the alkylated cyclohexylbenzene compound with a sulfonating reagent; forming a sulfonated reaction product; and converting the sulfonated reaction product into a sulfonate salt.

22 Claims, 1 Drawing Sheet

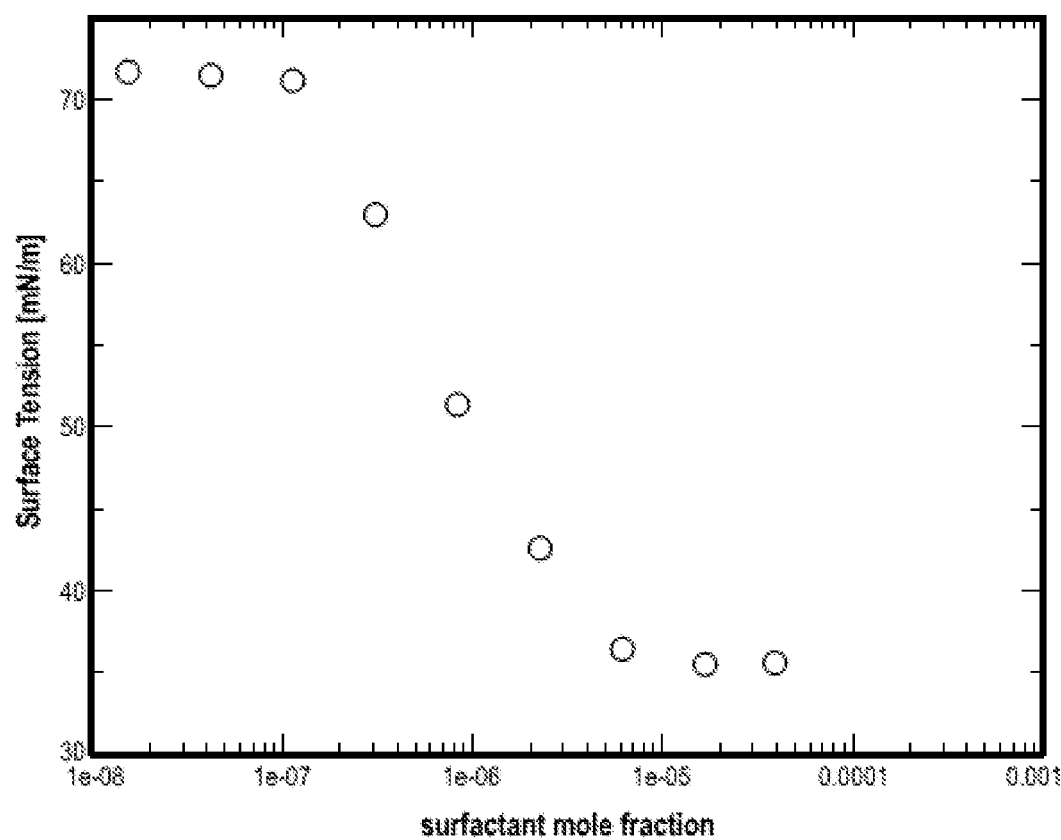

AMPHIPHILIC CYCLOHEXYLBENZENE COMPOUNDS DERIVED FROM ALPHA OLEFINS OR VINYLIDENE ALPHA OLEFIN DIMERS

CROSS-REFERENCE OF RELATED APPLICATIONS

This application claims the benefit of U.S. Provisional Application No. 62/898,172, filed Sep. 10, 2019, the disclosure of which is incorporated herein by reference.

BACKGROUND

Surfactants are compounds that tend to lower the surface tension at an interface between two components. As such, surfactants may be used in a wide range of applications, which may include, for example, promoting solubility of an otherwise sparingly soluble solid, lowering viscosity of a fluid phase, and promoting foaming of a fluid. Surfactants may be found in a wide range of consumer and industrial products including, for example, soaps, detergents, cosmetics, pharmaceuticals, and dispersants.

Surfactants feature both hydrophobic and hydrophilic portions within their molecular structure. As such, surfactants are amphiphilic. Hydrophobic portions are generally non-ionic and may include saturated or unsaturated hydrocarbyl groups, such as alkyl, alkenyl, or aryl groups. Hydrophilic portions, in contrast, feature polar head groups that may be ionic, non-ionic, or zwitterionic and encompass a range of polar functional groups or moieties. Ionic functional groups that may be present in the hydrophilic portion of surfactants include, for example, sulfonates, sulfates, carboxylates, phosphates, quaternary ammonium groups, and the like. Non-ionic hydrophilic portions may include functional groups or moieties bearing one or more heteroatoms that are capable of receiving hydrogen bonds, such as polyethers (e.g., ethoxylates). Zwitterionic hydrophilic portions may include moieties such as betaines, sultaines, and related phospholipid compounds.

Surfactants finding extensive commercial use generally feature a relatively limited range of structure types. Common classes of commercial surfactants include, for example, alkylbenzene sulfonates, lignin sulfonates, long chain fatty alcohol sulfates, long chain fatty acid carboxylates, long chain fatty alcohol ethoxylates, long chain quaternary ammonium compounds, and alkylphenol ethoxylates. The various classes of surfactants may exhibit a range of surfactant properties, and there may be further property variation within the members or homologues within each class. Accordingly, a surfactant for a given application may be chosen based upon various application-specific requirements. There remains a need, however, for development of additional types of surfactants having additional structural diversity and multifunctionality to accommodate presently unmet or unknown application-specific requirements within various industries.

References of interest include J. Favre, "Synthesis for detergent additives for lubricants. II. Study by infrared absorption spectrometry", in 10 REV. INST. FRANC. PETROLE 470-476 (1955); and WO 2009/085964.

SUMMARY

Compositions described herein may comprise a sulfonated reaction product or a salt thereof prepared from a cyclohexylbenzene compound that has been alkylated with an olefin having a structure represented by Formula 1;

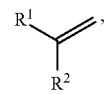

Formula 1 wherein $R^1$ is a $C_6$-$C_{24}$ hydrocarbyl group, and $R^2$ is H or a $C_6$-$C_{24}$ hydrocarbyl group. An olefinic carbon of the olefin becomes saturated and bonds to the cyclohexylbenzene compound once the cyclohexylbenzene compound has become alkylated.

Methods described herein may comprise contacting an alkylated cyclohexylbenzene compound having a structure represented by Formula 2 with a sulfonating reagent;

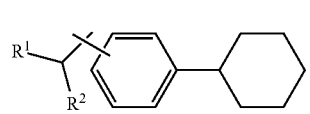

Formula 2 wherein $R^1$ is a $C_6$-$C_{24}$ hydrocarbyl group, and $R^2$ is H or a $C_6$-$C_{24}$ hydrocarbyl group; forming a sulfonated reaction product having a structure represented by Formula 3;

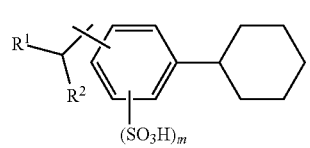

Formula 3 wherein m is an integer ranging from 0 to 4; and converting the sulfonated reaction product into a sulfonate salt.

Compositions described herein may comprise a sulfonated reaction product or a salt thereof having a structure represented by Formula 4;

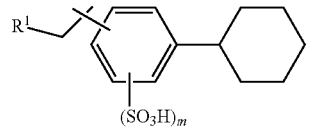

Formula 4 wherein m is an integer ranging from 0 to 4; and wherein $R^1$ is a $C_6$-$C_{24}$ hydrocarbyl group.

Compositions described herein may comprise a sulfonated reaction product or a salt thereof having a structure represented by Formula 3;

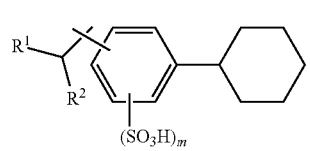

Formula 3 wherein m is an integer ranging from 0 to 4; and wherein $R^1$ and $R^2$ are each $C_6$-$C_{24}$ hydrocarbyl groups.

BRIEF DESCRIPTION OF THE DRAWINGS

The following FIGURE is included to illustrate certain aspects of the present disclosure, and should not be viewed as an exclusive embodiment. The subject matter disclosed is capable of considerable modifications, alterations, combinations, and equivalents in form and function, as will occur to one of ordinary skill in the art and having the benefit of this disclosure.

The FIGURE shows a graph of surface tension (nM/m) as a function of concentration (mole fraction) for the product of Example 3.

DETAILED DESCRIPTION

The present disclosure generally relates to amphiphilic compounds and, more specifically, to amphiphilic compounds formed from alpha olefins or vinylidene alpha olefin dimers and methods for production thereof.

As discussed above, most surfactants in common commercial use are based upon a relatively limited number of chemical structural classes. The various structural classes, as well as specific members or homologues within each structural class, may exhibit a range of surfactant properties, which may be chosen for suitability or compatibility with a given application. Some existing and emerging applications may have application-specific needs that are not adequately met by presently available surfactants.

The present disclosure describes amphiphilic compounds comprising a cyclohexylbenzene scaffold that are reaction products of alpha olefins or vinylidene alpha olefin dimers with a cyclohexylbenzene compound, which may exhibit useful surfactant properties. The reaction products may be referred to as "amphiphilic cyclohexylbenzene compounds" hereinafter. Alpha olefins of various sizes are commercially available in great volume at very low cost. Vinylidene alpha olefin dimers may be readily prepared through dimerizing two alpha olefins, which may be the same or different. The reaction product may be formed through alkylation of the phenyl ring of the cyclohexylbenzene compound with the alpha olefins or the vinylidene alpha olefin dimers, such as through an electrophilic aromatic addition reaction of an olefin moiety therein.

Amphiphilic cyclohexylbenzene compounds of the present disclosure feature a hydrophobic portion including an alkylated cyclohexylbenzene group, and a hydrophilic portion comprising a polar head group appended (bonded) directly to the hydrophobic portion, specifically to the phenyl ring of the alkylated cyclohexylbenzene group. Surfactants formed via alkylation of a cyclohexylbenzene compound with an alpha olefin or a vinylidene alpha olefin dimer, followed by sulfonation of the alkylated cyclohexylbenzene group, may be particularly advantageous because of the structural diversity of olefins or dimers thereof that may be used to alkylate the phenyl ring of the cyclohexylbenzene compound, as well as the variety of possible geometric arrangements of the hydrophilic and hydrophobic moieties therein. Alkylation and sulfonation may be carried out readily in high yields. As such, a range of amphiphilic compounds comprising an alkylated cyclohexylbenzene group having tailored surfactant properties may be accessed inexpensively and in a straightforward manner using the disclosure herein.

Alpha olefins and vinylidene alpha olefin dimers may have various chain lengths and may or may not contain branches, such as a limited amount of methyl or ethyl branches (e.g., at most, one branch per alpha olefin or two branches per vinylidene alpha olefin dimer). The chain length and branching or lack thereof may impact various surfactant properties such as packing factor, which is the ratio of the volume of the hydrophobic portion to an interfacial area occupied by the hydrophilic portion and the length of the hydrophobic portion. The surface activity of an amphiphilic compound may also be impacted by the functionalities (chemical moieties, chain length, presence or absence of branching) within the hydrophobic portion.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbons or hydrocarbyl groups may be one or more of linear, branched, cyclic, acyclic, saturated, unsaturated, aliphatic, or aromatic.

The terms "saturated" or "saturated hydrocarbon" refer to a hydrocarbon or hydrocarbyl group in which all carbon atoms are bonded to four other atoms or bonded to three other atoms with one unfilled valence position thereon.

The terms "unsaturated" or "unsaturated hydrocarbon" refer to a hydrocarbon or hydrocarbyl group in which one or more carbon atoms are bonded to less than four other atoms, optionally with one unfilled valence position on the one or more carbon atoms.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The term "alkyl" refers to a hydrocarbyl group having no unsaturated carbon-carbon bonds, and which may be optionally substituted. The term "alkylene" refers to an alkyl group having at least two open valence positions.

The term "alkenyl" refers to a hydrocarbyl group having a carbon-carbon double bond, and which may be optionally substituted. The terms "alkene" and "olefin" may be used synonymously herein. Similarly, the terms "alkenic" and "olefinic" may be used synonymously herein. Unless otherwise noted, all possible geometric and positional isomers are encompassed by these terms.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms.

Examples of saturated hydrocarbyl groups include, but are not limited to, methyl, ethyl, n-propyl, isopropyl, n-butyl, isobutyl, sec-butyl, tert-butyl, pentyl, isopentyl, hexyl, octyl, cyclopropyl, cyclobutyl, cyclopentyl, cyclohexyl, cyclooctyl, and the like, including their substituted analogues. Examples of unsaturated hydrocarbyl groups include, but are not limited to, ethenyl, propenyl, allyl, butadienyl, cyclopropenyl, cyclobutenyl, cyclopentenyl, cyclohexenyl, cyclooctenyl and the like, including their substituted analogues.

Examples of aromatic hydrocarbyl groups include, but are not limited to, phenyl, tolyl, xylyl, naphthyl, and the like, including all possible isomeric forms thereof. Polynuclear aromatic hydrocarbyl groups may include, but are not limited to, naphthalene, anthracene, indane, and indene.

The terms "oligomer(s)" and "oligomeric product" refer to a molecule having a predetermined number of repeating monomer units, where the number of repeating monomer units is relatively small and specifiable. Illustrative oligomers include dimers, trimers, tetramers, higher oligomers, and mixtures thereof. The term "oligomerization process" refers to any process of catalytically joining monomer units together to form an oligomer or oligomers. The term "oligomerization conditions" refers to any and all variations of equipment, reaction conditions (e.g., temperatures, pressures, and/or flow rates), materials, and reactor configurations that are suitable to conduct an oligomerization process.

The terms "linear" and "linear hydrocarbon" refer to a hydrocarbon or hydrocarbyl group having a continuous carbon chain without side chain branching, in which the continuous carbon chain may be optionally substituted with heteroatoms or heteroatom groups.

The terms "branch," "branched" and "branched hydrocarbon" refer to a hydrocarbon or hydrocarbyl group having a linear main carbon chain in which a hydrocarbyl side chain extends from the linear main carbon chain. Optional heteroatom substitution may be present in the linear main carbon chain or in the hydrocarbyl side chain. Conversely, the term "unbranched" refers to a hydrocarbon or hydrocarbyl group having a linear main carbon chain without any hydrocarbyl side chain extending from the linear main carbon chain. The term "substantially unbranched" refers to a hydrocarbon or hydrocarbyl group having a linear main carbon chain without any hydrocarbyl side chain extending from the linear main carbon chain or with hydrocarbyl side chain extending from the linear main carbon chain in a trace amount relative to the mass of compound containing the main carbon chain, such as one or two methyl or ethyl branches per main carbon chain.

The term "amphiphilic compound" refers to a compound having both a hydrophobic portion and a hydrophilic portion featuring a polar head group. The terms "polar head group" and "hydrophilic portion" may be synonymously herein.

The term "vinylidene" refers to an olefin moiety bearing two hydrogen atoms upon C-1 and two hydrocarbyl groups upon C-2 of the olefin moiety.

The term "trisubstituted" refers to an olefin moiety bearing two hydrocarbyl groups upon a first carbon atom of the olefin moiety and one hydrocarbyl group and one hydrogen atom upon a second carbon atom of the olefin moiety, wherein the olefin moiety is non-terminal.

The acronym "CMC" refers to critical micelle concentration given in wt. %, where surface tension becomes independent of the surfactant concentration.

The acronym "ST" refers to surface tension, typically given in millinewtons (mN) per meter.

The acronyms "$Kv_{100}$" and "$Kv_{100}$" refer to the kinematic viscosity at 100° C. and 40° C. of a fluid, and are typically given in centistokes (cSt).

The acronym "VI" refers to the viscosity index of a fluid.

Advantageously, alpha olefins and vinylidene alpha olefin dimers may be used in the alkylation of cyclohexylbenzene compounds to form reaction products that may be subsequently sulfonated and reacted in the presence of a base to provide compounds that may have surfactant properties. The alkylation of cyclohexylbenzene with an alpha olefin or a vinylidene alpha olefin dimer in presence of a catalyst is shown in Reaction 1.

Reaction 1

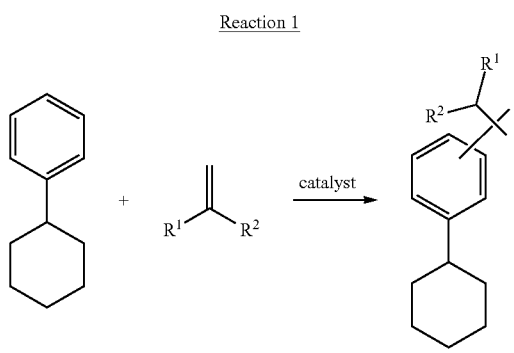

The sulfonation of the alkylated cyclohexylbenzene compound produced in Reaction 1 is shown in Reaction 2. In this reaction scheme, m is an integer ranging from 0 to 4.

Reaction 2

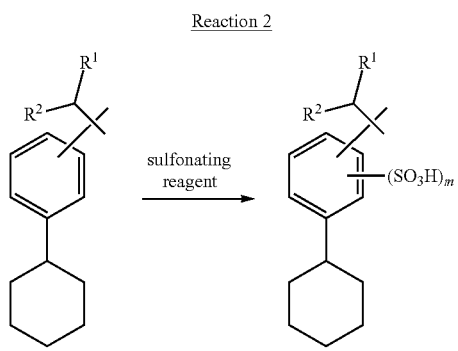

After obtaining the sulfonated reaction product of Reaction 2, the sulfonic acid group(s) may be neutralized with a base, such as sodium hydroxide, to produce an alkylated cyclohexylbenzene sulfonate, as shown in Reaction 3.

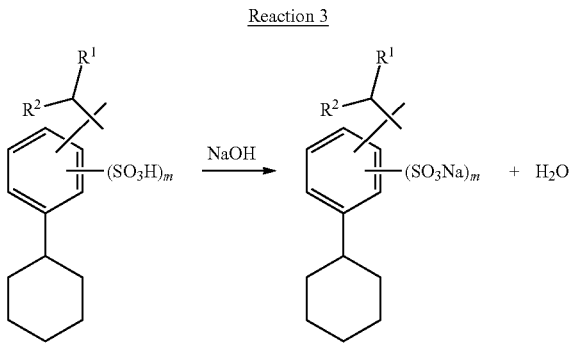

Reaction 3

Alpha olefins and vinylidene alpha olefin dimers suitable for use in forming the amphiphilic cyclohexylbenzene compounds of the present disclosure may be represented by Formula 1 below.

Formula 1

$R^1$ is a hydrocarbyl group, preferably a $C_6$-$C_{24}$ hydrocarbyl group. For an alpha olefin, $R^2$ is H. For a vinylidene alpha olefin dimer, $R^2$ is a hydrocarbyl group, preferably a $C_6$-$C_{24}$ hydrocarbyl group. $R^1$ and $R^2$ may be of the same length, or they may be of differing lengths. For example, if $R^1$ and $R^2$ are both hydrocarbyl groups, thereby defining a vinylidene olefin dimer, $R^1$ and $R^2$ may each be $C_6$-$C_{18}$ or $C_{12}$-$C_{18}$ or $C_{18}$-$C_{24}$ hydrocarbyl groups. Optional methyl and/or ethyl branching may be present within $R^1$ and $R^2$. Alpha olefins having one methyl or ethyl branch per $R^1$ may also be considered to constitute linear alpha olefins for purposes of the present disclosure. Similarly, a vinylidene alpha olefin dimer having one methyl or ethyl branch per $R^1$ and/or $R^2$ may be considered to have been formed from a linear alpha olefin. Carbon atoms within the branches are not included in the total carbon count of the alpha olefins and vinylidene alpha olefin dimers described herein. As such, suitable alpha olefins may contain from about 8 to about 26 carbon atoms, and suitable vinylidene alpha olefin dimers may contain from about 14 to about 50 carbon atoms, not including any carbons contributed by methyl or ethyl branches. Preferably, $R^1$ and $R^2$ are substantially unbranched.

Alpha olefins may be synthesized by several different processes starting from low molecular weight olefins. The primary route for synthesizing alpha olefins is via ethylene oligomerization, of which there are several synthetic variants that may be mediated using different Ziegler-type catalysts. Depending on the particular Ziegler-type catalyst and the synthetic conditions, ethylene oligomerization reactions may form a range of homologous alpha olefins having an even number of carbon atoms (i.e., $C_2$—$H_2$—, where n is a positive integer greater than or equal to 2), or a predominant alpha olefin (e.g., 1-octene, 1-decene, 1-undecene, 1-tetradecene, 1-hexadecene, or 1-octadecene) may be produced. Preferably, linear alpha olefins may be formed in the presence of the Ziegler-type catalyst.

The reaction to form vinylidene alpha olefin dimers may be promoted by various metallocene catalyst systems. Catalyst systems suitable for oligomerizing alpha olefins into vinylidene alpha olefin dimers may comprise a metallocene catalyst system, for example, a bis(cyclopentadienyl)zirconium(IV) dichloride ($Cp_2ZrCl_2$), in combination with a suitable activator. Other non-limiting examples of metallocene catalysts that may be suitable to form vinylidene alpha olefin dimers include, for example, bis-(n-propylcyclopentadienyl) zirconium(IV) dichloride, bis(1-butyl-3-methylcyclopentadienyl) zirconium dichloride, Schwartz's reagent (zirconocene chloride hydride), or rac-dimethylsilyl-bis-(tetrahydroindenyl) zirconium dimethyl, each in combination with a suitable activator such as an alumoxane (e.g., methylalumoxane-MAO) or a non-coordinating anion activator. Still other suitable metallocene catalysts that may be used for synthesizing vinylidene alpha olefin dimers may be found in commonly owned U.S. Patent Application Publication 2018/0282359, which is incorporated herein by reference in its entirety.

A non-coordinating anion (NCA) is defined to mean an anion either that does not coordinate to a transition metal center or that does coordinate to a transition metal center, but only weakly. The term NCA is defined to include multicomponent NCA-containing activators, such as N,N-dimethylanilinium tetrakis(pentafluorophenyl)borate and N,N-dimethylanilinium tetrakis(heptafluoronaphthyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. Other NCAs may also be suitable for use in forming vinylidene alpha olefin dimers. Typically, NCAs coordinate weakly enough that a neutral Lewis base, such as an olefin can displace it from the metal center, thereby forming a catalytically active species. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. The term non-coordinating anion includes neutral activators, ionic activators, and Lewis acid activators.

Particularly suitable NCAs may include, for example, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, triphenylcarbenium tetra(perfluorophenyl) borate, or any combination thereof.

The general structure of alkylated cyclohexylbenzene compounds formed according to the present disclosure is represented by Formula 2A below. The alkylated cyclohexylbenzene compounds are produced by alkylating the aromatic ring of a cyclohexylbenzene with an alpha olefin or a vinylidene alpha olefin dimer having the structure represented by Formula 1 above.

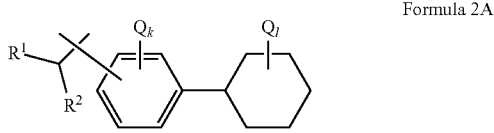

Formula 2A $R^1$ and $R^2$ are defined as above for the alpha olefin or vinylidene alpha olefin dimer used to form the alkylated cyclohexylbenzene compound. In Formula 2A, Q is a non-hydrogen substituent, preferably a hydrocarbyl group, k is an integer ranging from 0 to 4 and 1 is an integer ranging from 0 to 5. In a particular example, Q is absent from each phenyl ring (k and 1 are both 0), as illustrated in the alkylated cyclohexylbenzene compound represented by Formula 2B. In other examples, each Q may be a methyl group (1=m=1) in various positions on the phenyl or cyclohexyl rings, as illustrated in the alkylated cyclohexylbenzene compounds represented by Formulas 2C-2H.

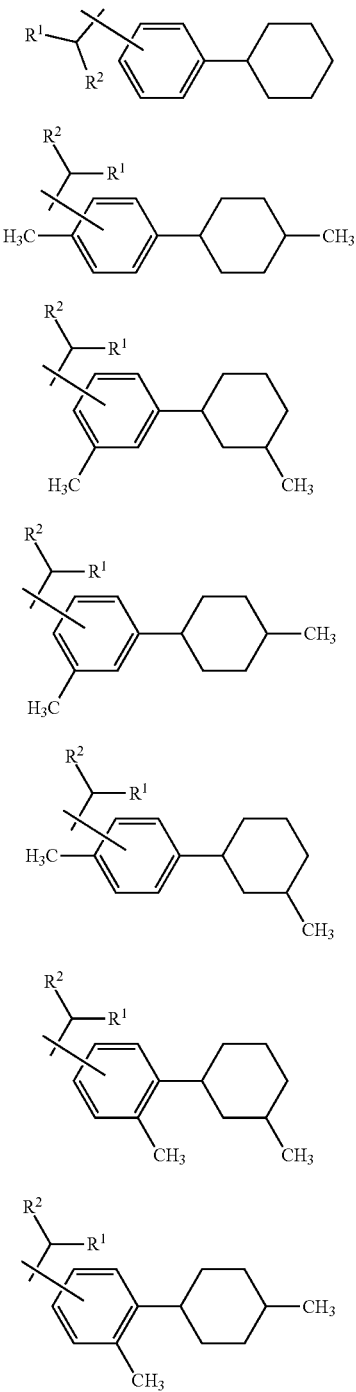

Thus, for alkylated cyclohexylbenzene compounds formed from alpha olefins, $R^2$ is H and for alkylated cyclohexylbenzene compounds formed from vinylidene alpha olefin dimers, $R^2$ is a hydrocarbyl group, preferably a $C_6$-$C_{24}$ hydrocarbyl group. Upon alkylation of the cyclohexylbenzene compound, one olefinic carbon of the alpha olefin or vinylidene alpha olefin dimer reacts electrophilically with the aromatic ring of the cyclohexylbenzene compound to become saturated and bond to the aromatic ring. Alkylation may occur upon either the terminal or non-terminal carbon atom of the olefin functional group, but alkylation may typically occur upon the non-terminal carbon atom due to carbocation rearrangement during alkylation.

Alkylation of cyclohexylbenzene compounds may be carried out using acid alkylation catalysts (e.g., Friedel-Crafts catalysts and similar catalyst types). These catalysts may result in mixtures of monoalkylated and polyalkylated products as the acid catalyst may isomerize and oligomerize the olefin and alkylation may occur at multiple positions on the aromatic rings of the cyclohexylbenzene compound. Advantageously, solid molecular sieve catalysts may provide alkylated cyclohexylbenzene compounds with better controlled alkylation locations on the cyclohexylbenzene compound and without the need for further purification, separation and additional work-up. Suitable alkylation catalysts that may be used in the alkylation process of the present disclosure include MCM-49, MCM-56, MCM-36, MCM-22, MCM-41, UZM-8, USY, PSH-3, SSZ-25, Mordenite, ZSM-12, CBV 760, Amberlyst-15, $AlCl_3$, acidic ionic liquids, $SO_4$-doped silica, and clay. Catalyst choice may influence the predominant product isomer formed. The alkylation of cyclohexylbenzene compounds may be conducted such that the organic reactants (i.e., the cyclohexylbenzene compound and the alpha olefin or vinylidene alpha olefin dimer) are brought into contact with a suitable catalyst in a reactor under effective alkylation conditions. Such conditions are known in the art, and may vary based upon the catalyst used. Suitable reaction temperatures may range from about 0° C. to about 500° C., preferably from about 50° C. to about 250° C. Suitable pressures may range from about 0.2 atmospheres to about 250 atmospheres, preferably from about 5 atmospheres to about 100 atmospheres. The molar ratio of cyclohexylbenzene compound to alpha olefin or vinylidene alpha olefin dimer may range from about 0.1:1 to about 50:1, preferably from about 0.5:1 to about 10:1.

Unreacted cyclohexylbenzene compound and olefin(s), if present, may be removed by distillation or heating under vacuum before moving to subsequent steps in forming the amphiphilic compounds described herein. That is, after alkylation takes place, unreacted cyclohexylbenzene compounds and/or olefins may be removed before conducting a sulfonation reaction.

The alkylated cyclohexylbenzene compound obtained by reacting the cyclohexylbenzene compound and an alpha olefin or a vinylidene alpha olefin dimer may then be contacted with a suitable sulfonating reagent. Conventional sulfonating reagents such as oleum, concentrated $H_2SO_4$, $SO_3$ gas, $SO_3$ in solvent or $SO_3$/dioxane complex may be used to promote the sulfonation reaction. However, these reagents may be prone to producing sultones, and the reverse desulfonation reaction may occur under the reaction conditions.

A non-conventional sulfonating reagent that may be advantageous for conducting the sulfonation reaction in the present disclosure is silica-sulfuric acid. Silica-sulfuric acid may be prepared by contacting silica gel with chlorosulfonic acid to form a stable reagent capable of transferring sulfonate groups when contacted with an aromatic compound. The sulfonation reaction with silica-sulfuric acid may occur neat (without solvent) or in the presence of a solvent that is not itself subject to sulfonation, such as 1,2-dichloroethane. With this sulfonating reagent, the sulfonation reaction may occur at temperatures in a range from about 20° C. to about 120° C., preferably from about 50° C. to about 100° C. Advantageously, silica-sulfuric acid promotes sulfonation with high selectivity, such that occurrence of the reverse desulfonation reaction is low and sultone production is similarly suppressed. Without being bound by theory or mechanism, the selectivity of silica-sulfuric acid is believed to result from the relatively large molecular size of this reagent. Since silica-sulfuric acid is a solid sulfonation reagent, isolation of the sulfonated reaction product may be conducted easily by filtration or decantation, for example. After recovering the silica-sulfuric acid, the reagent may be recycled through several additional reaction cycles without losing substantial catalytic activity.

After obtaining the sulfonated reaction product, the sulfonic acid group may be neutralized with a base, such as a hydroxide base, preferably an alkali metal hydroxide base, to produce an alkylated cyclohexylbenzene sulfonate. The attachment site of the sulfonate substituent on the aromatic ring of the cyclohexylbenzene may vary among product isomers.

In view of the foregoing, compositions of the present disclosure may comprise a sulfonated reaction product or a salt thereof prepared from a cyclohexylbenzene compound that has been alkylated with an olefin having a structure represented by Formula 1. As specified above, $R^1$ may be a $C_6$-$C_{24}$ hydrocarbyl group, and $R^2$ may be H or a $C_6$-$C_{24}$ hydrocarbyl group. An olefinic carbon of the olefin becomes saturated and bonds to the cyclohexylbenzene compound once the cyclohexylbenzene compound has become alkylated.

The sulfonated reaction product, which may comprise one or more amphiphilic cyclohexylbenzene compounds, is an alkylated cyclohexylbenzene compound that has been further sulfonated. The sulfonate groups may be bonded to the aromatic ring of the cyclohexylbenzene compound which is also alkylated. As such, sulfonated reaction products of the present disclosure may have a structure represented by Formulas 3A and 3B below.

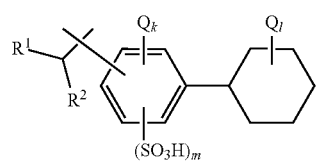

Formula 3A

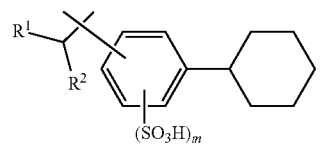

Formula 3B

In Formulas 3A and 3B above, m is an integer ranging from 0 to 4. In Formula 3A, Q is a non-hydrogen substituent, preferably a hydrocarbyl group, k is an integer ranging from 0 to 4 and l is an integer ranging from 0 to 10. In a particular example, Q is absent from each ring (k and l are both 0), as illustrated in Formula 3B. In particular examples, m ranges from 1 to 4, and is preferably 1.

In particular examples, the olefin that has alkylated the cyclohexylbenzene compound is an alpha olefin, such that $R^2$ is H. When $R^2$ is H, $R^1$ may be a $C_6$-$C_{24}$ alkyl group, which may be substantially unbranched and/or bear one methyl or ethyl branch, in a more specific example of the present disclosure. Such alkylated cyclohexylbenzene compounds may be employed in any embodiment of the present disclosure.

Accordingly, some compositions of the present disclosure may comprise a sulfonated reaction product or a salt thereof having a structure represented by Formula 4.

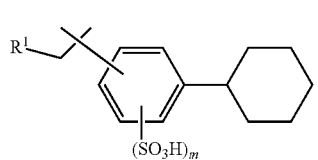

Formula 4

In Formula 4, $R^1$ is a $C_6$-$C_{24}$ hydrocarbyl group, preferably a $C_{12}$-$C_{18}$ alkyl group, which may be substantially unbranched or bear one methyl or ethyl branch, and more preferably a substantially unbranched $C_{12}$ alkyl group. Variable m is an integer ranging from 0 to 4. In particular examples, m ranges from 1 to 4, and is preferably 1.

In other particular examples, the olefin that has alkylated the cyclohexylbenzene compound is a vinylidene alpha olefin dimer, such that $R^2$ is a $C_6$-$C_{24}$ hydrocarbyl group. In a more specific example of the present disclosure, $R^1$ and $R^2$ may each be $C_6$-$C_{24}$ alkyl groups, preferably $C_6$-$C_{12}$ alkyl groups, which may independently be substantially unbranched and/or bear one methyl or ethyl branch. Such alkylated cyclohexylbenzene compounds may be employed in any embodiment of the present disclosure.

When the vinylidene alpha olefin dimer is prepared by dimerizing a single alpha olefin, $R^1$ and $R^2$ have a different number of carbon atoms. For example, when 1-decene is dimerized to the corresponding vinylidene alpha olefin dimer, $R^1$ has 8 carbon atoms and $R^2$ has 10 carbon atoms. When the vinylidene alpha olefin dimer is prepared by dimerizing two different alpha olefins, $R^1$ and $R^2$ have the same number of carbon atoms or a different number of carbon atoms. When dimerizing two different alpha olefins, mixtures of different vinylidene alpha olefins may be obtained.

Accordingly, some compositions of the present disclosure may comprise a sulfonated reaction product or a salt thereof having a structure represented by Formula 2, in which $R^1$ and $R^2$ are each $C_6$-$C_{24}$ hydrocarbyl groups, preferably a $C_6$-$C_{12}$ alkyl group, which may be substantially unbranched or bear one methyl or ethyl branch. $R^1$ and $R^2$ may have the same number of carbon atoms or a different number of carbon atoms, depending on the alpha olefins used to form the vinylidene alpha olefin dimer. Even more preferably, $R^1$ is a substantially unbranched $C_8$ alkyl group and $R^2$ is a substantially unbranched $C_{10}$ alkyl group. Variable m is an integer ranging from 0 to 4. In particular examples, m ranges from 1 to 4, and is preferably 1.

In view of the foregoing, methods for making the amphiphilic cyclohexylbenzene compounds of the present disclosure may comprise: contacting an alkylated cyclohexylbenzene compound having a structure represented by Formula 2 with a sulfonating reagent, forming a sulfonated reaction product having a structure represented by Formula 3, and converting the sulfonated reaction product into a sulfonate salt. As defined above, $R^1$ is a $C_6$-$C_{24}$ hydrocarbyl group and $R^2$ is H or a $C_6$-$C_{24}$ hydrocarbyl group. Variable m is an integer ranging from 0 to 4. Preferably, m is 1.

In a particular example, the sulfonating reagent may be silica-sulfuric acid. Any amount of the sulfonating reagent above a stoichiometric amount may be used.

The methods for making the amphiphilic compounds may further comprise separating the sulfonated reaction product from the sulfonating reagent. In the case where the sulfonating reagent is silica-sulfuric acid, separation may take place by filtration or decantation.

The foregoing sulfonated reaction products derived from alpha olefins or vinylidene alpha olefin dimers may be formulated in solid form or dispersed or dissolved in a fluid phase to afford formulated surfactants for use in various applications. Surfactants of the present disclosure may comprise an aqueous fluid, in which one or more sulfonated reaction products described herein are dissolved or dispersed, preferably in an amount of about 10 wt. % to about 80 wt. %. Suitable aqueous fluids are not particularly limited and may be selected from deionized water, tap water, fresh water, surface water, ground water, brackish water, salt water, sea water, brine, or any combination thereof. Other aqueous fluid sources may also be suitable. The aqueous fluid may further comprise a water-miscible organic solvent such as one or more alcohols, for example, in some embodiments. When dissolved in a suitable aqueous fluid, the reaction products disclosed herein may exhibit a range of surfactant properties. According to some embodiments, the reaction products may be present in the aqueous fluid above a critical micelle concentration.

Embodiments disclosed herein include:

A. Compositions comprising one or more amphiphilic alkylated cyclohexylbenzene compounds. The compositions comprise: a sulfonated reaction product or a salt thereof prepared from a cyclohexylbenzene compound that has been alkylated with an olefin having a structure represented by Formula 1;

Formula 1 wherein $R^1$ is a $C_6$-$C_{24}$ hydrocarbyl group, and $R^2$ is H or a $C_6$-$C_{24}$ hydrocarbyl group; and
wherein an olefinic carbon of the olefin becomes saturated and bonds to the cyclohexylbenzene compound once the cyclohexylbenzene compound has become alkylated.

B. Methods for sulfonating alkylated cyclohexylbenzene compounds. The methods comprise: contacting an alkylated cyclohexylbenzene compound having a structure represented by Formula 2 with a sulfonating reagent;

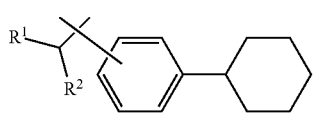

Formula 2 wherein $R^1$ is a $C_6$-$C_{24}$ hydrocarbyl group, and $R^2$ is H or a $C_6$-$C_{24}$ hydrocarbyl group;
forming a sulfonated reaction product having a structure represented by Formula 3;

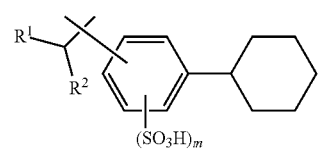

Formula 3 wherein m is an integer ranging from 0 to 4; and converting the sulfonated reaction product into a sulfonate salt.

C. Compositions comprising one or more amphiphilic cyclohexylbenzene compounds derived from alpha olefins. The compositions comprise: A composition comprising: a sulfonated reaction product or a salt thereof having a structure represented by Formula 4;

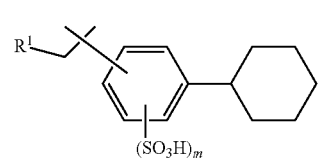

Formula 4 wherein m is an integer ranging from 0 to 4; and wherein $R^1$ is a $C_6$-$C_{24}$ hydrocarbyl group.

D. Compositions comprising one or more amphiphilic cyclohexylbenzene compounds derived from vinylidene alpha olefin dimers. The compositions comprise: A composition comprising: a sulfonated reaction product or a salt thereof having a structure represented by Formula 3;

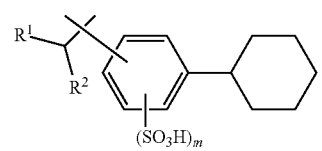

Formula 3 wherein m is an integer ranging from 1 to 4; and wherein $R^1$ and $R^2$ are each $C_6$-$C_{24}$ hydrocarbyl groups.

Each of embodiments A, B, C, and D may have one or more of the following additional elements in any combination:

Element 1: wherein the sulfonated reaction product has a structure represented by Formula 3 or a salt thereof;

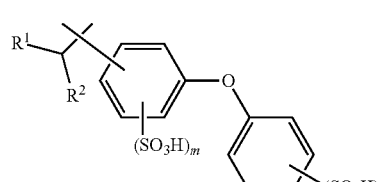

Formula 3 wherein m is an integer ranging from 0 to 4 and n is an integer ranging from 0 to 5, and m+n is 1 or greater.

Element 2: wherein m is 1.
Element 3: wherein $R^2$ is H.
Element 4: wherein $R^1$ is a $C_6$-$C_{24}$ alkyl group.
Element 5: wherein the $C_6$-$C_{24}$ alkyl group is substantially unbranched.

Element 6: wherein $R^1$ and $R^2$ are each $C_6$-$C_{24}$ alkyl groups.

Element 7: wherein $R^1$ and $R^2$ have a different number of carbon atoms.

Element 8: wherein the $C_6$-$C_{24}$ alkyl groups are substantially unbranched.

Element 9: wherein the sulfonating reagent is silica-sulfuric acid.

Element 10: wherein $R^1$ is a substantially unbranched $C_{12}$ alkyl group.

Element 11: wherein $R^1$ is a substantially unbranched $C_8$ alkyl group and $R^2$ is a substantially unbranched $C_{10}$ alkyl group.

By way of non-limiting example, exemplary combinations applicable to A, B, C or D include, but are not limited to, Element 2 in combination with one or more of Elements 3 to 4; Element 4 in combination with Element 5; Element 1 in combination with one or more of Elements 2, 3, and 6; Element 7 in combination with Elements 8 and 9; Element 4 in combination with Element 10; and Element 6 with Element 11.

To facilitate a better understanding of the embodiments described herein, the following examples of various representative embodiments are given. In no way should the following examples be read to limit, or to define, the scope of the present disclosure.

EXAMPLES

Example 1

A 100 mL sealed thick round bottomed flask was charged with 2.0 g MCM-49 catalyst, phenylcyclohexane (10 g, 0.06239 mol, 1 eq) and 1-tetradecene (18.4 g, 0.06239 mole, 1.5 eq). The reaction mixture was stirred overnight at 130° C. The heterogeneous mixture was then filtered and washed with 50 mL toluene. The toluene solvent was removed under reduced pressure with a rotary evaporator. The high-boiling unreacted 1-tetradecene was removed in a vacuum oven under high vacuum at 130° C. A $C_{14}$ alkylated cyclohexylbenzene compound represented by Formula 5 was obtained with a yield of 11.60 g (about 37%). The isolated product was characterized by $^1$H NMR and FTIR. The product $^1$H NMR showed both phenyl peaks at 7.23-6.91 ppm and alkyl peaks at 2.65-0.85 ppm. IR: 3021, 2924, 2852, 1603, 1486, 1449, 1377, 1349, 998, 878, 824, 792, 751, 421, and 706 $cm^{-1}$.

Formula 5

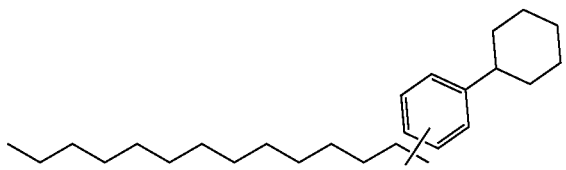

Lubricant properties ($Kv_{40}$, $Kv_{100}$ and VI) of the alkylated cyclohexylbenzene were determined and are shown in Table 1. The data illustrates that the alkylated cyclohexylbenzene had a high viscosity index, particularly as compared to that of a $C_{14}$ alkylated biphenyl reference compound. In a non-limiting example, KV and VI may be measured using ASTM D445 and ASTM D2272, respectively.

TABLE 1

| Fluid | Olefin | Aromatic Group | $Kv_{100}$ (cSt) | $Kv_{40}$ (cSt) | VI |
|---|---|---|---|---|---|
| 1 | 1-tetradecene | Biphenyl | 4.69 | 31.4 | 37 |
| 2 | 1-tetradecene | Phenylcyclohexane | 4.65 | 25.2 | 99 |

Example 2

The $C_{14}$ alkylated cyclohexylbenzene compound of Example 1 was sulfonated by charging a 100 mL round bottomed flask with 44% silica sulfuric acid (12.54 g, 0.0563 mol, 4.0 eq.) and the $C_{14}$ alkylated cyclohexylbenzene compound (5 g, 0.0140 mole, 1 eq) in 1,2-dichloroethane (40 mL). The reaction mixture was stirred at 93° C. for 18 h. The heterogeneous mixture then filtered and washed with dichloromethane (50 mL) to remove unreacted $C_{14}$ alkylated cyclohexylbenzene. The resulting sulfonated $C_{14}$ alkylated cyclohexylbenzene product was collected by washing the heterogeneous mixture with methanol (50 mL). The sulfonated $C_{14}$ alkylated cyclohexylbenzene product was characterized by 41 NMR. The sulfonated $C_{14}$ alkylated cyclohexylbenzene was sparingly soluble in water.

Example 3

The sulfonated reaction product of Example 2 was converted to the corresponding sodium salt by dissolving 4 g of the sulfonated $C_{14}$ alkylated cyclohexylbenzene in 50 mL methanol (pH about 4.0) at 10-15° C. 50% aqueous NaOH (2.5 g) solution was slowly added to precipitate the pale yellow sodium salt of the sulfonated $C_{14}$ alkylated cyclohexylbenzene (pH about 7.0-8.0). The reaction mixture was stirred for 1 h and filtered, and the residue was washed with 15 mL methanol. The isolated product was dried overnight at 60° C. in a vacuum oven and characterized by IR. The $C_{14}$ alkylated cyclohexylbenzene sulfonate sodium salt product was sparingly soluble in water and surface active.

Example 4

Surface tension isotherms were measured for the product of Example 3. Surface tension data was collected using a Kruss K100 force tensiometer. The measurements were made using the Wilhelmy plate method with a platinum plate at a temperature of approximately 23° C. The surface tension isotherm data, shown in The FIGURE demonstrate that the $C_{14}$ alkylated cyclohexylbenzene sulfonate sodium salt provides a highly effective and efficient surfactant product.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure.

Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A composition comprising a sulfonated reaction product or a salt thereof prepared from a cyclohexylbenzene compound that has been alkylated with an olefin having a structure represented by Formula 1;

Formula 1 wherein $R^1$ is a $C_6$-$C_{24}$ hydrocarbyl group, and $R^2$ is H or a $C_6$-$C_{24}$ hydrocarbyl group; and wherein, in the sulfonated reaction product or salt thereof, an olefinic carbon of the olefin is saturated and bonded to a phenyl ring of the cyclohexylbenzene compound once the cyclohexylbenzene compound has become alkylated.

2. The composition of claim 1, wherein the sulfonated reaction product has a structure represented by Formula 3 or a salt thereof;

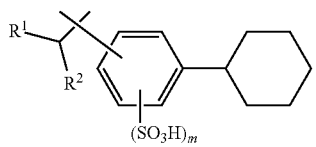

Formula 3 wherein m is an integer ranging from 1 to 4.

3. The composition of claim 2, wherein m is 1.
4. The composition of claim 1, wherein $R^2$ is H.
5. The composition of claim 1, wherein $R^1$ is a $C_6$-$C_{24}$ alkyl group.
6. The composition of claim 5, wherein the $C_6$-$C_{24}$ alkyl group is substantially unbranched.
7. The composition of claim 1, wherein $R^1$ and $R^2$ are each $C_6$-$C_{24}$ alkyl groups.
8. The composition of claim 7, wherein $R^1$ and $R^2$ have a different number of carbon atoms.
9. The composition of claim 7, wherein the $C_6$-$C_{24}$ alkyl groups are substantially unbranched.
10. A method comprising contacting an alkylated cyclohexylbenzene compound having a structure represented by Formula 2 with a sulfonating reagent;

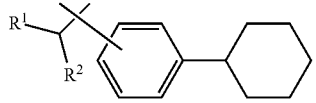

Formula 2 wherein $R^1$ is a $C_6$-$C_{24}$ hydrocarbyl group, and $R^2$ is H or a $C_6$-$C_{24}$ hydrocarbyl group;

forming a sulfonated reaction product having a structure represented by Formula 3;

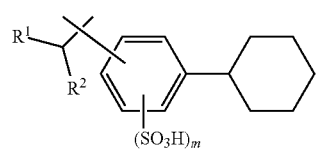

Formula 3 wherein m is an integer ranging from 1 to 4; and
converting the sulfonated reaction product into a sulfonate salt.

11. The method of claim 10, wherein the sulfonating reagent is silica-sulfuric acid.
12. The method of claim 10, wherein m is 1.
13. The method of claim 10, wherein $R^2$ is H.
14. The method of claim 10, wherein $R^1$ is a $C_6$-$C_{24}$ alkyl group.
15. The method of claim 14, wherein the $C_6$-$C_{24}$ alkyl group is substantially unbranched.
16. The method of claim 10, wherein $R^1$ and $R^2$ are each $C_6$-$C_{24}$ alkyl groups.
17. The method of claim 16, wherein $R^1$ and $R^2$ have a different number of carbon atoms.
18. The method of claim 16, wherein the $C_6$-$C_{24}$ alkyl groups are substantially unbranched.
19. A composition comprising a sulfonated reaction product or a salt thereof having a structure represented by Formula 4;

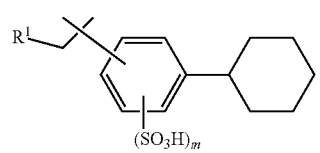

Formula 4 wherein m is an integer ranging from 1 to 4; and
wherein $R^1$ is a $C_6$-$C_{24}$ hydrocarbyl group.

20. The composition of claim 19, wherein m is 1.
21. The composition of claim 19, wherein $R^1$ is a $C_{12}$-$C_{24}$ alkyl group.
22. The composition of claim 19, wherein $R^1$ is a substantially unbranched $C_{12}$ alkyl group.

* * * * *